US009512000B2

(12) United States Patent
Chang et al.

(10) Patent No.: US 9,512,000 B2
(45) Date of Patent: Dec. 6, 2016

(54) FABRICATION AND SELF-ALIGNED LOCAL FUNCTIONALIZATION OF NANOCUPS AND VARIOUS PLASMONIC NANOSTRUCTURES ON FLEXIBLE SUBSTRATES FOR IMPLANTABLE AND SENSING APPLICATIONS

(71) Applicant: CALIFORNIA INSTITUTE OF TECHNONOLGY, Pasadena, CA (US)

(72) Inventors: Chieh-feng Chang, Pasadena, CA (US); Sameer Walavalkar, Studio City, CA (US); Scott E. Fraser, Glendale, CA (US); Axel Scherer, Barnard, VT (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/952,876

(22) Filed: Nov. 25, 2015

(65) Prior Publication Data
US 2016/0158724 A1 Jun. 9, 2016

Related U.S. Application Data

(60) Provisional application No. 62/089,724, filed on Dec. 9, 2014.

(51) Int. Cl.
| | | |
|---|---|---|
| *C23F 1/00* | (2006.01) | |
| *B81C 1/00* | (2006.01) | |
| *H01L 21/02* | (2006.01) | |

(Continued)

(52) U.S. Cl.
CPC ....... *B81C 1/00476* (2013.01); *B81C 1/00468* (2013.01); *B82Y 40/00* (2013.01); *H01L 21/02164* (2013.01); *H01J 37/3053* (2013.01);

(Continued)

(58) Field of Classification Search
CPC .......... B81C 1/00468; B81C 1/00476; B82Y 40/00; H01J 37/3053; H01J 2237/3174; H01J 2237/3053; H01L 21/02164; H01L 41/332
USPC ............. 216/2, 11, 43, 66, 79; 438/723, 725
See application file for complete search history.

(56) References Cited

U.S. PATENT DOCUMENTS 8,080,468 B2 12/2011 Scherer et al.
2007/0243519 A1 10/2007 Hess et al.
(Continued)

FOREIGN PATENT DOCUMENTS

EP 2653530 A2 10/2013
JP 2004-286570 A 10/2004
(Continued)

OTHER PUBLICATIONS

Walavalkar, S et al. "Scalable Method for the Fabrication and Testing of Glass-Filled, Three-Dimensionally Sculpted Extraordinary Transmission Apertures." Nano Lett. vol. 14 (1), pp. 311-317 2014.

(Continued)

*Primary Examiner* — Binh X Tran
(74) *Attorney, Agent, or Firm* — Steinfl & Bruno, LLP (57) ABSTRACT

Methods for fabricating flexible substrate nanostructured devices are disclosed. The nanostructures comprise nanopillars and metallic bulbs or nano-apertures. The nanostructures can be functionalized to detect biological entities. The flexible substrates can be rolled into cylindrical tubes for detection of fluidic samples.

26 Claims, 10 Drawing Sheets (51) Int. Cl.
*B82Y 40/00* (2011.01)
*H01L 41/332* (2013.01)
*H01L 21/3213* (2006.01)
*H01J 37/305* (2006.01)

(52) U.S. Cl.
CPC .. *H01J 2237/3174* (2013.01); *H01L 21/32137* (2013.01); *H01L 41/332* (2013.01)

(56) References Cited

U.S. PATENT DOCUMENTS

| | | |
|---|---|---|
| 2008/0032420 A1 | 2/2008 | Lambert et al. |
| 2009/0215050 A1 | 8/2009 | Jenison |
| 2010/0066346 A1 | 3/2010 | Zhang et al. |
| 2010/0085566 A1 | 4/2010 | Cunningham |
| 2011/0053794 A1 | 3/2011 | Zhang |
| 2011/0116089 A1 | 5/2011 | Schmidt et al. |
| 2011/0128536 A1 | 6/2011 | Bond et al. |
| 2012/0105853 A1* | 5/2012 | Pang ............... G03H 1/02 356/445 |
| 2012/0135260 A1* | 5/2012 | Jang ............... C25D 5/022 428/546 |
| 2012/0142119 A1 | 6/2012 | Zhang et al. |
| 2012/0287427 A1 | 11/2012 | Li et al. |
| 2013/0090536 A1 | 4/2013 | Milner et al. |
| 2013/0236881 A1 | 9/2013 | Spatz et al. |
| 2014/0024131 A1 | 1/2014 | Kim et al. |
| 2014/0037920 A1* | 2/2014 | Kobrin ............ C03C 17/23 428/210 |
| 2014/0199778 A1 | 7/2014 | Wu et al. |
| 2014/0293280 A1* | 10/2014 | Kohnke ........... G01N 21/658 356/301 |
| 2015/0194549 A1* | 7/2015 | Weman ......... H01L 31/022466 136/244 |
| 2015/0223738 A1 | 8/2015 | Walavalkar et al. |
| 2015/0223739 A1 | 8/2015 | Walavalkar et al. |
| 2015/0253321 A1* | 9/2015 | Chou .............. G01N 33/54366 435/5 |

FOREIGN PATENT DOCUMENTS

| | | |
|---|---|---|
| WO | 2012/024006 A2 | 2/2012 |
| WO | 2013/158114 A1 | 10/2013 |
| WO | 2014/021809 A1 | 2/2014 |

OTHER PUBLICATIONS

Barman, I. et al. "Accurate Spectroscopic Calibration for Noninvasive Glucose Monitoring by Modeling the Physiological Glucose Dynamics." Anal. Chem. 82, pp. 6104-6114. 2010.
Henry, M.D., et al. "Alumina etch masks for the fabrication of high-aspect-ratio silicon micropillars and nanopillars." Nanotechnology, vol. 20, 255305, pp. 1-4. 2009.
Walavalkar, S.S., et al. "Controllable deformation of silicon nanowires with strain up to 24%." Journal of Applied Physics, vol. 107, 124314, pp. 1-5. 2010.
Walavalkar, S.S., et al. "Tunable visible and near-Ir emission from sub-10 nm etched single crystal Si nanopillars." Nano Letters, 2010. vol. 10, p. 4423-4428.
Walavalkar, S.S., et al. "Size tunable visible and near-infrared photoluminescence from vertically etched silicon quantum dots." Applied Physics Letters, 2011.vol. 98, pp. 153114-153117.
Walavalkar, S.S., et al. "Three-dimensional etching of silicon for the fabrication of low-dimensional and suspended devices." Nanoscale, 2013. vol. 5, pp. 927-931.
Walavalkar, S.S., et al. "Coulomb blockade in vertical, bandgap engineered silicon nanopillars." Applied Physics Letters, 2013. vol. 102, 183101, pp. 1-3.
Walavalkar, S.S., et al. "Scalable method for the fabrication and testing of glass-filled, three- dimensionally sculpted extraordinary transmission apertures." Nano letters, 2014. vol. 14, pp. 311-317.

Wulfkuhle, J.D., et al. "Proteomic applications for the early detection of cancer." Nature reviews. Cancer, 2003, vol. 3, pp. 267-275.
Dalby, T. et al. "Laboratory diagnosis of pertussis: agglutination is not suitable." Respirology (Carlton, Vic.), 2011. vol. 6, pp. 1160-1162.
Campbell, H., et al., "Oral fluid testing for pertussis, England and Wales, Jun. 2007-Aug. 2009." Emerging Infectious Diseases, 2014. vol. 20, pp. 968-975.
Rasooly, A., et al. "Development of biosensors for cancer clinical testing." Biosensors & Bioelectronics, 2006. vol. 21, pp. 1851-1858.
Soper, S.A., et al. "Point-of-care biosensor systems for cancer diagnostics/prognostics." Biosensors & Bioelectronics, 2006. vol. 21, pp. 1932-1942.
Wang, J., "Electrochemical biosensors: towards point-of-care cancer diagnostics." Biosensors & Bioelectronics, 2006.vol. 21: pp. 1887-1892.
Wei, F., et al. "Electrochemical sensor for multiplex biomarkers detection." Clinical Cancer Research, 2009. vol. 15: pp. 4446-4452.
Tothill, I.E. "Biosensors for cancer markers diagnosis." Seminars in Cell & Developmental Biology, 2009. vol. 20: pp. 55-62.
Lozano, R., et al. "Global and regional mortality from 235 causes of death for 20 age groups in 1990 and 2010: a systematic analysis for the Global Burden of Disease Study 2010." Lancet, 2012. vol. 380, pp. 2095-2128.
Howlader N, N.A., et al. SEER Cancer Statistics Review, 1975-2011, 2014: National Cancer Institute. Bethesda, MD.
Shah, F.D. et al. "A review on salivary genomics and proteomics biomarkers in oral cancer." Indian Journal of Clinical Biochemistry : IJCB, 2011. vol. 26: pp. 326-334.
Punyani, S.R. et al. "Salivary level of interleukin-8 in oral precancer and oral squamous cell carcinoma." Clinical Oral Investigations, 2013. vol. 17, pp. 517-524.
Cheng, Y.S.L., et al. "A review of research on salivary biomarkers for oral cancer detection." Clinical and Translational Medicine, 2014. vol. 3,10 pg.
Tondella, M.L., et al., "International Bordetella pertussis assay standardization and harmonization meeting report. Centers for Disease Control and Prevention, Atlanta, Georgia, United States, Jul. 19-20, 2007." Vaccine, 2009. vol. 27: pp. 803-814.
Melvin, J.A., et al. "Bordetella pertussis pathogenesis: current and future challenges." Nature Reviews. Microbiology, 2014. vol. 12: pp. 274-288.
Atwell, J.E., et al. "Nonmedical vaccine exemptions and pertussis in California, 2010." Pediatrics, 2013.vol. 132: pp. 624-630.
Locht, C. "Molecular aspects of Bordetella pertussis pathogenesis, in International Microbiology." vol. 2, pp. 137-144. 1999.
de Gouw, D., et al. "Pertussis: a matter of immune modulation." FEMS microbiology reviews, 2011. vol. 35: pp. 441-474.
Shembekar, V.R., et al. "A protecting group for carboxylic acids that can be photolyzed by visible light." Biochemistry, 2005. vol. 44: pp. 7107-7114.
Kumar, S., et al. "Directional conjugation of antibodies to nanoparticles for synthesis of multiplexed optical contrast agents with both delivery and targeting moieties." Nature protocols, 2008. vol. 3: pp. 314-320.
Li, Y. et al. "Salivary transcriptome diagnostics for oral cancer detection." Clinical Cancer Research: an official journal of the American Association for Cancer Research. 2004. vol. 10: p. 8442-8450.
Sung, H.J., et al. "Inhibition of human neutrophil activity by an RNA aptamer bound to interleukin-8." Biomaterials, 2014. vol. 35: pp. 578-589.
Ellington, A.D. et al. "In vitro selection of RNA molecules that bind specific ligands." Nature, 1990. vol. 346: pp. 818-822.
Hamaguchi, N., et al. "Aptamer beacons for the direct detection of proteins." Analytical Biochemistry, 2001. vol. 294, pp. 126-131.
Roberts, R.W., et al. "RNA-peptide fusions for the in vitro selection of peptides and proteins." Proceedings of the National Academy of Sciences, 1997. vol. 94: pp. 12297-12302.
Takahashi, T.T., et al. "mRNA display: ligand discovery, interaction analysis and beyond." Trends in Biochemical Sciences, 2003.vol. 28: pp. 159-165.

(56) References Cited

OTHER PUBLICATIONS

Wilson, D.S., et al. "The use of mRNA display to select high-affinity protein-binding peptides." Proceedings of the National Academy of Sciences of the United States of America, 2001. vol. 98: pp. 3750-3755.

Aoyama, T. et al. "Comparison of blood-free medium (cyclodextrin solid medium) with Bordet-Gengou medium for isolation clinical ion of Bordetella pertussis." J. Clin. Microbiol., 1986. vol. 23: pp. 1046-1048.

Yang, X., et al. "Construction and selection of bead-bound combinatorial oligonucleoside phosphorothioate and phosphorodithioate aptamer libraries designed for rapid PCR-based sequencing." Nucleic Acids Research, 2002. vol. 30: e132, 8 pgs.

Goldman, W.E., et al. "Detection, isolation, and analysis of a released Bordetella pertussis product toxic to cultured tracheal cells." Infect. Immun., 1982. vol. 36: pp. 782-794.

Rosenthal, R.S., et al., "Major fragment of soluble peptidoglycan released from growing Bordetella pertussis is tracheal cytotoxin." Infect. Immun., 1987. vol. 55: pp. 2117-2120.

Leavitt, A.J., et al. "Chemical reactive studies of hydrogen sulfide on Au(111)." Surface Science, 1994. vol. 314: pp. 22-33.

Kim, D-H et al. "Flexible and Stretchable Electronics for Biointegrated Devices," *Annu. Rev.* 14, pp. 113-128 (2012).

Lo, J.C. et al. "Fabrication of a large, ordered, three-dimensional nanocup array," *App. Phys. Lett.* 101 (8), p. 081109 (2012).

Mishra, Y.K. et al. "Formation of Self-organized Silver Nanocup-Type Structures and Their Plasmonic Absorption," *Plasmonics* 8, pp. 811-815 (2013).

Wang, Z. et al. "Synthesis and magnetic properties of large-area ferromagnetic cylindrical nanoshell and nanocup arrays," *J Phys. Chem.* 113 (21), p. 214301 (2013).

International Search Report mailed on May 26, 2015 for PCT/US2015/015693 filed on Feb. 12, 2015 in the name of California Institute of Technology.

Written Opinion mailed on May 26, 2015 for PCT/US2015/015693 filed on Feb. 12, 2015 in the name of California Institute of Technology.

International Search Report mailed on May 28, 2015 for PCT/US2015/015698 filed on Feb. 12, 2015 in the name of California Institute of Technology.

Written Opinion mailed on May 28, 2015 for PCT/US2015/015698 filed on Feb. 12, 2015 in the name of California Institute of Technology.

International Search Report mailed on May 28, 2015 for PCT/US2015/015701 filed on Feb. 12, 2015 in the name of California Institute of Technology.

Written Opinion mailed on May 28, 2015 for PCT/US2015/015701 filed on Feb. 12, 2015 in the name of California Institute of Technology.

International Search Report mailed on May 29, 2015 for PCT/US2015/015705 filed on Feb. 12, 2015 in the name of California Institute of Technology.

Written Opinion mailed on May 29, 2015 for PCT/US2015/015705 filed on Feb. 12, 2015 in the name of California Institute of Technology.

International Search Report and Written Opinion for International Application No. PCT/US2015/062804 filed Nov. 25, 2015 on behalf of California Institute of Technology. Mail Date: May 17, 2016. 13 pages.

* cited by examiner

FABRICATION AND SELF-ALIGNED LOCAL FUNCTIONALIZATION OF NANOCUPS AND VARIOUS PLASMONIC NANOSTRUCTURES ON FLEXIBLE SUBSTRATES FOR IMPLANTABLE AND SENSING APPLICATIONS

CROSS REFERENCE TO RELATED APPLICATIONS

The present application claims priority to U.S. Provisional Patent Application No. 62/089,724, filed on Dec. 9, 2014, and may be related to U.S. Patent Publication No. U.S. 2015-0223738 A1, published Aug. 13, 2015, U.S. Patent Publication No. U.S. 2015-0223739 A1, published on Aug. 13, 2015, U.S. patent application Ser. No. 14/621,295, filed on Feb. 12, 2015, and U.S. patent application Ser. No. 14/621,306, filed on Feb. 12, 2015, the disclosure of each of which is incorporated herein by reference in its entirety.

TECHNICAL FIELD

The present disclosure relates to plasmonic nanostructures. More particularly, it relates to the fabrication and self-aligned local functionalization of nanocups and various plasmonic nanostructures on flexible substrates for implantable and sensing applications.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, a method is described, the method comprising: etching a silicon substrate to form silicon nanostructures on top of the silicon substrate; oxidizing the silicon nanostructures to form silicon oxide nanostructures; depositing a metallic layer on the silicon oxide nanostructures; reflowing the metallic layer to form metallic bulbs on a top section of the silicon oxide nanostructures; depositing a continuous flexible substrate on the metallic bulbs and on the silicon oxide nanostructures; and removing the silicon substrate and the silicon oxide nanostructures.

In a second aspect of the disclosure, a method is described, the method comprising: etching a silicon substrate to form silicon nanostructures on top of the silicon substrate; oxidizing the silicon nanostructures to form silicon oxide nanostructures; depositing a metallic layer on the silicon oxide nanostructures; reflowing the metallic layer to form metallic bulbs on a top section of the silicon oxide nanostructures; depositing a continuous flexible substrate on the metallic bulbs and on the silicon oxide nanostructures; and removing the silicon substrate and the silicon oxide nanostructures.

In a third aspect of the disclosure, a method is described, the method comprising: etching a silicon substrate to form silicon nanostructures on top of the silicon substrate; oxidizing the silicon nanostructures to form silicon oxide nanostructures; depositing a metallic layer on the silicon oxide nanostructures; reflowing the metallic layer to form metallic bulbs on a top section of the silicon oxide nanostructures; depositing a photosensitive layer on the metallic bulbs and on the silicon oxide nanostructures; selecting an intensity for optical excitation to be above an excitation threshold only for the photosensitive layer between the metallic bulbs; optically exciting at the selected intensity; removing the excited photosensitive layer, thereby leaving gaps in the photosensitive layer between the metallic bulbs; and functionalizing the gaps between the metallic bulbs.

DETAILED DESCRIPTION

The present disclosure describes several methods for transferring metal nanostructures onto flexible substrates for plasmonic applications. For example, by depositing a flexible layer on top of a structure and removing the original substrate, it is possible to obtain nanocups. It is also possible to choose whether to keep metal between the different nanostructures. The distance between nanostructures can be adjusted by stretching or compressing the flexible substrate. With a sacrificial layer, it is possible to control how close the nanocups are to the surface of the flexible layer. With a carrier chip, the nanostructures can also be transferred onto a flexible layer in an upright position. In embodiments with a carrier chip, it is also possible to optionally remove the metal between the nanostructures, for optical excitation from the opposite side of the chip relative to the nanostructures. The shapes of these nanostructures can be tailored by multiple stages of oxidation and etching, by the reflow process, by ion treatment (optionally at an angle), by angled deposition, and by an arbitrary combination of these techniques. For closely-spaced metal nanostructures, it is possible to take advantage of local field enhancement to achieve self-aligned functionalization through either development or ablation. With a carrier chip or with appropriate etching, the transferred nanostructures can reside in a cavity of a flexible substrate, which can be used for implantation in biological tissue, or for wearable applications. On the other hand, the flexible substrate can also be bended to decrease the distance between nanostructures, or rolled into a tube as a channel for liquid samples to flow through. In the latter case, the central channel can also function as a waveguide for either optical excitation or signal waves. With proper design, the nanostructures can also be rolled up in a spiral fashion for extended interaction areas. Many of the techniques described in the present disclosure can also apply to nano-apertures from similar Si templates.

Recently, Walavalkar et al. demonstrated a technique that allows wafer-scalable fabrication of metal nanostructures for plasmonic applications, see Ref [1]. Unlike focus ion beam (FIB) approaches, which are time-consuming and restricted by their capacity for beam focusing, the methods described in the present disclosure requires procedures that are already available in a commercial semiconductor foundry for mass production. Unlike another previous approach of metal lift-off, which is limited by lithography resolution and cannot accommodate a thick layer of deposition, with the methods described in the present disclosure nanostructures can be directly fabricated with great precision and a high aspect ratio. Additionally, with the methods described herein, a designer has freedom to choose where to place the structures on a chip, unlike methods based on metal nanocrystals via bottom-up synthesis. Several applications are possible for the methods of the present disclosure, such as functionalized assays, on-chip imaging via extraordinary transmission, surface-enhanced Raman spectroscopy (SERS), etc., for sensing and implantation purposes, see Refs. [2, 3].

In several applications of sensing and implantation, a rigid substrate can be a limiting factor in terms of conformity, immunity rejection, device versatility, etc. A sensor based on flexible substrates is therefore very desirable. Flexible substrates, however, can be problematic in fabrication since they may not be compatible with some fabrication procedures such as thermal treatment. The present disclosure describes methods for fabricating metal nanostructures on flexible substrates, in order to render the structures better suited for certain sensing and implantation applications. The methods described herein also allow the fabrication of devices types that were previously unavailable, such as nanocups with an optional background layer of metal between structures.

Figure 1:
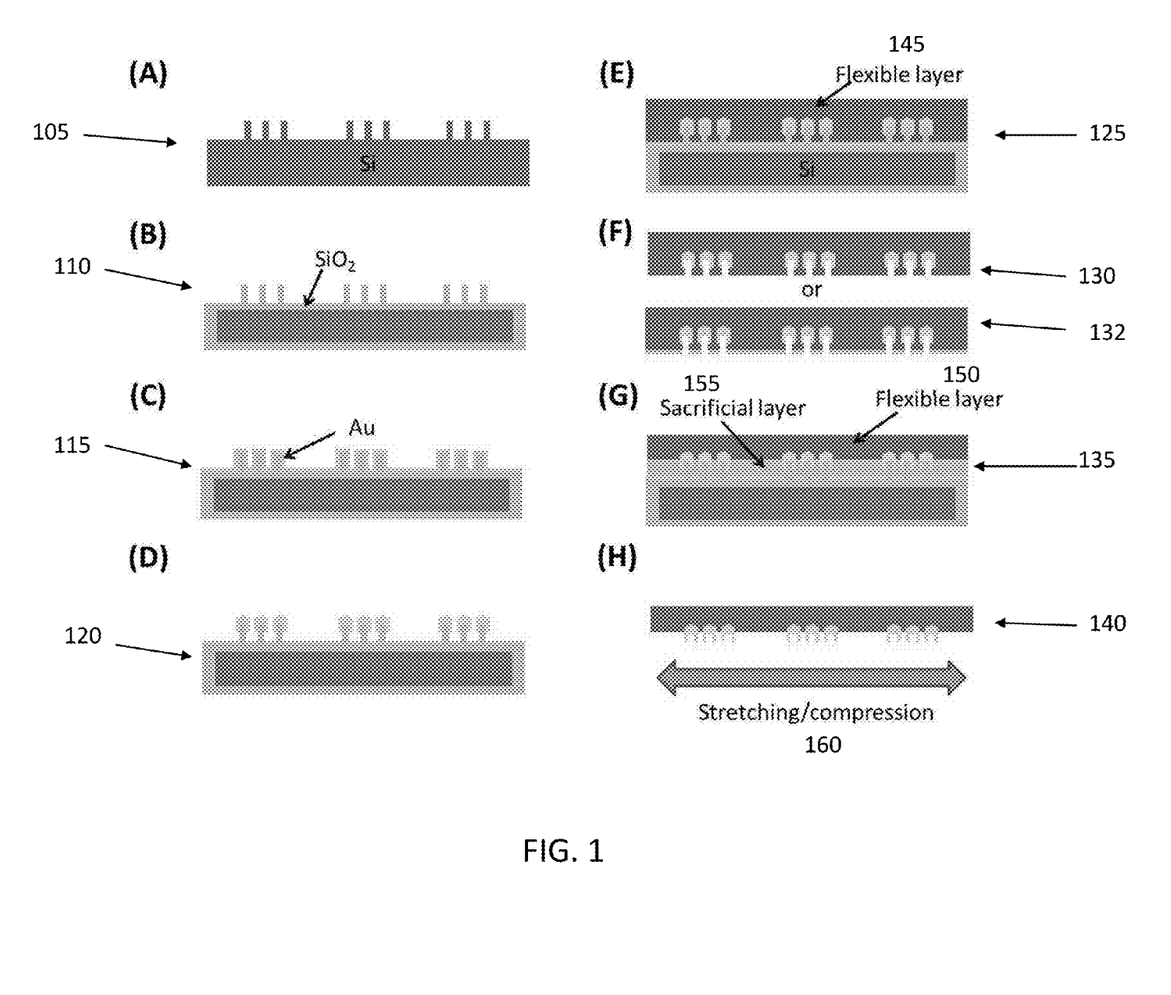
FIG. 1 illustrates a method of fabrication of nanostructures with a flexible substrate.

The fabrication and chip processing of closely-spaced metal nano-spheres for surface-enhanced Raman spectroscopy (SERS) applications have been described in previous disclosures, see Refs. [1-3]. Briefly, as visible in FIG. 1, nanostructures can be defined on Si substrates, for example by pseudo Bosch etching (105), followed by thermal oxidation (110), and a metal is then deposited (115) and reflowed (120). For example, gold can be used. Starting with such structures, a flexible layer (145) can then be deposited on top of the chip (125). For example, polydimethylsiloxane (PDMS) can be used; other options can include, and are not limited to, polymers, plastics, etc. The flexible layer is then detached from the substrate (130); options include mechanical peel-off, chemical etching that does not attack the flexible membrane during the processing time, etc. The hollow interiors of the nano-spheres, previously attached to the glass pillars, are now exposed as nanocups. Previously nanocups had been fabricated using nano-indentation, see Ref. [4], lift-off with sacrificial layers, see Ref [5], metal deposition on nano-beads, see Ref [6], and substrate treatment for self-organized structures, see Ref. [7]. These methods have many disadvantages including lack of designer's freedom, low aspect ratio of structures, etc. In the technique presented herein it is possible to control where the nanostructures should be on a substrate, and shapes with a high aspect ratio can be easily achieved with etching control techniques, such as pseudo Bosch. The pseudo Bosch technique also allows 3D sculpting of the nanostructures, therefore the fabricated nanocups can take a variety of interior cavity shapes like rectangular, oval, etc, unlike highly-symmetric ones in previous literature documents, such as Refs. [4-7]. Depending on the thickness of the deposited metal and the reflow process (ramp-up/down rates, temperature, duration, etc.), it is also possible to control the final shape of the nanospheres that wick onto the top of the nanostructures, and hence further customize the final shape of the nanocups. For the areas between nanocups, moreover, previous approaches would either not use metal, or would result in metal deposition everywhere on the structure, while the method described herein can enable the choice of keeping or discarding the metal between the nanostructures.

Figure 2:
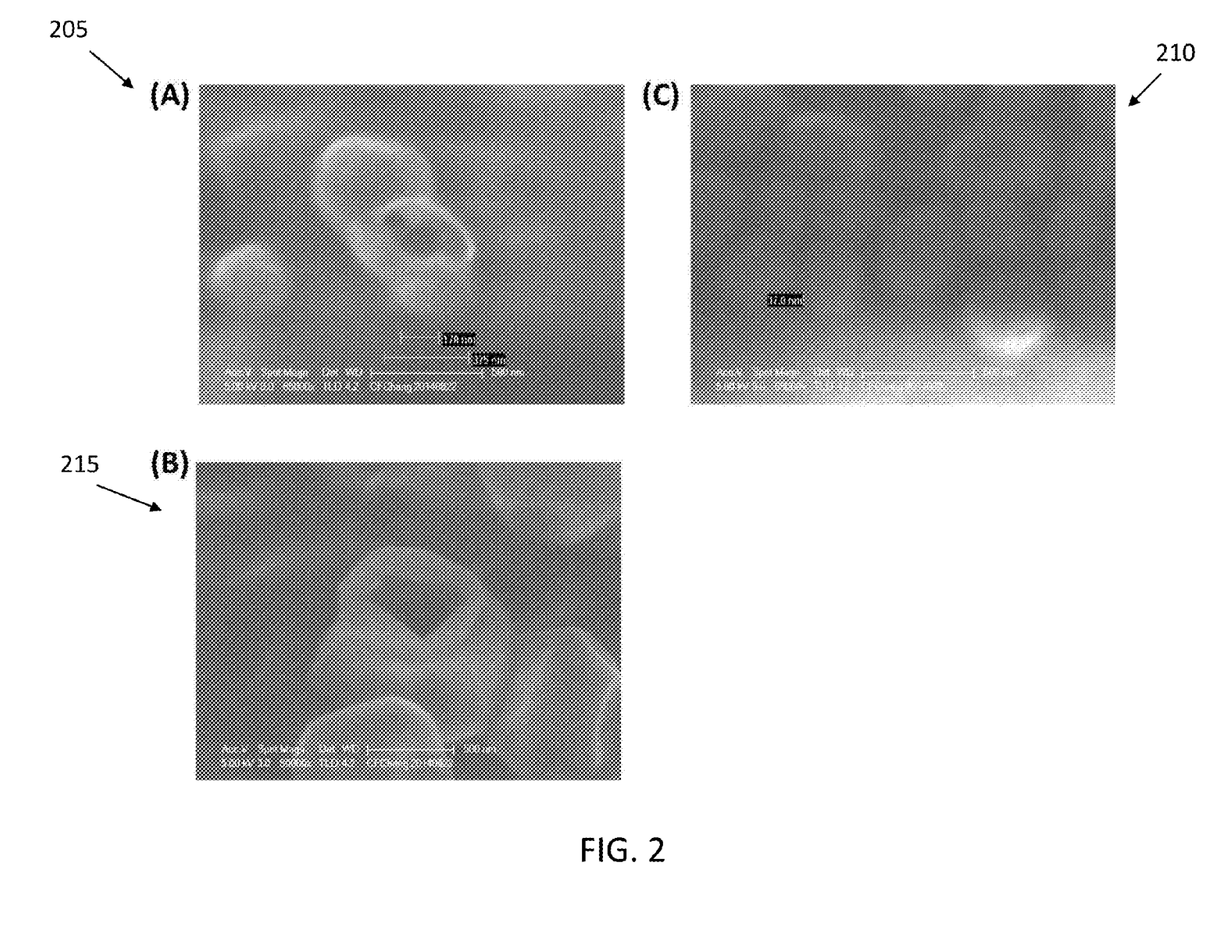
FIG. 2 illustrates SEM images of nanostructures.

If the choice is made to remove the regions of silicon and silicon dioxide with etching chemistry that does not affect the metal and the flexible layers, it is possible to optionally keep the metal in the region between nanocups as shown in (132). In the present technique, additionally, it is possible to precisely control how deeply the nanocups are embedded in the flexible substrate. Referring to (135), it is possible to first deposit a sacrificial layer (155) on top that can be etched with precision; an example of such a combination is photoresist and oxygen plasma ashing. After the sacrificial layer (155) is brought to the desired thickness, the flexible layer (150) can be applied on top as described earlier, followed by the separation of the flexible substrate along with embedded nanocups either mechanically or chemically into the configuration as depicted in (140). In this embodiment it is possible to take advantage of the small gaps between metal spheres, as well as the newly-exposed nanocup cavities after the separation of layers. The gaps between metal spheres can be controlled to be 10-20 nm or smaller, for example. Furthermore, the flexible layer (150, 140) can be manually stretched or compressed to modify the distance between metal nanostructures. Some exemplary fabrication results are shown in FIG. 2, which describes the embodiment of (140) in FIG. 1, where the metal structures are close to the surface of the non-conducting substrate for easier SEM (scanning electron microscope) imaging. FIG. 2 (205) shows a nanocup from a pillar structure. As described above, it is possible to tailor the nanocup shapes with great freedom, as shown in FIG. 2 (215) for a rectangular post. FIG. 2 (210) illustrates how it is possible to exploit the small gap between nanospheres in the methods described in the present disclosure.

Employing some additional steps as described below, it is possible to fabricate nanocups with an interior cavity much smaller than that typically allowed by lithography resolution. Starting from etched nanostructures as in FIG. 3 (305), the chips then go through a quick oxidation process either in a thermal furnace or a rapid thermal annealing (RTA) machine (310); the oxidation time is chosen so that the core of the Si nanostructures remains not oxidized. The outer layer of silicon oxide (312) is then removed (315), for example by hydrofluoric acid. The entire chip is then thermally treated again, this time for the entire nanostructures to be oxidized (320, 322). After depositing metal on a top surface of the device (325), including the nanostructures, the metal can be reflowed into nanospheres (330). For example the metal can be Au (327). In a subsequent step, the nanosphere structures can be converted into nanocups (FIG. 1, 130, 132, or 140) as described above. In some embodiments, the protruding nanostructures can be etched away or mechanically removed (FIG. 3, 335), for example for applications such as plasmonic assays or extraordinary transmission, see Ref [2]. In some embodiments, the openings in the metal layer are transparent to photons, and therefore can be termed as nano-tunnels (340), although these structures are filled with an oxide. In the present disclosure, nano-apertures can refer to different structures, for example in some embodiments nano-apertures are nano-cups (for example nano-cups that have a mushroom shape), while in other embodiments nano-apertures may be nano-tunnels, which are actually filled with an oxide but are still considered apertures for the incoming photons. In some embodiments, the glass opening in the midst of the metal film can be much smaller than lithography allows.

Figure 4:
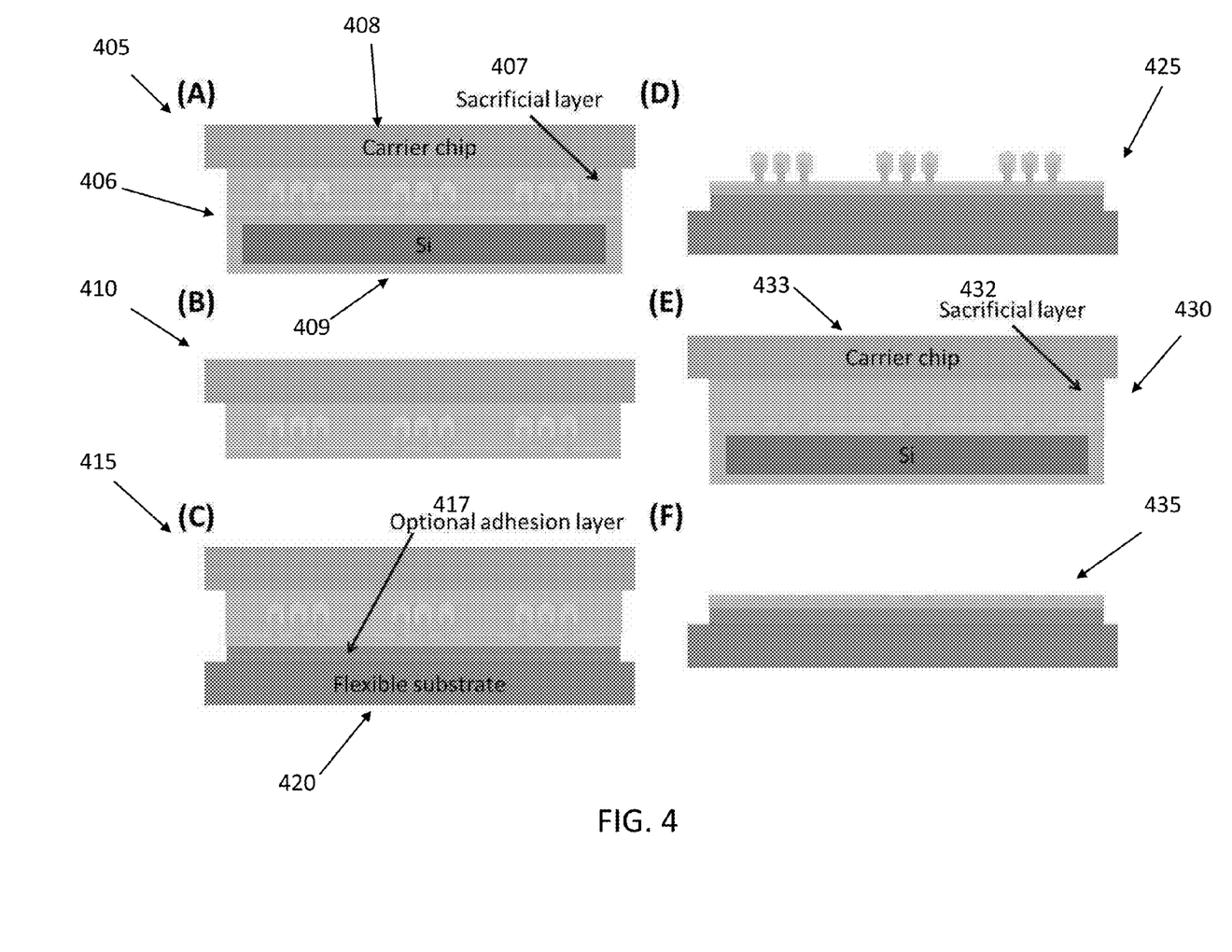
FIG. 4 illustrates a method of fabrication with a carrier chip.

In some embodiments, the structures can be transferred to flexible substrates. Referring to FIG. 4 (405), a sacrificial layer (407) is first deposited on top of the chip (406), and a carrier chip (408) is then attached to the sacrificial layer (407) for mechanical support in subsequent steps of processing. The substrate below the structures is then removed (410): First, the silicon region is exposed by etching away the bottom silicon dioxide layer (409), for example by hydrofluoric acid or by fluorocarbon plasma; the silicon can then be etched away with $XeF_2$, $SF_6$ plasma, or other methods. Depending on the flexible substrate of choice, an optional adhesion layer (417) can be applied to the now-exposed $SiO_2$ layer, and a flexible layer (420) is deposited or bonded onto the entire stack (415). The sacrificial layer is then etched away, thus releasing the carrier chip from the final structures (425).

Figure 3:
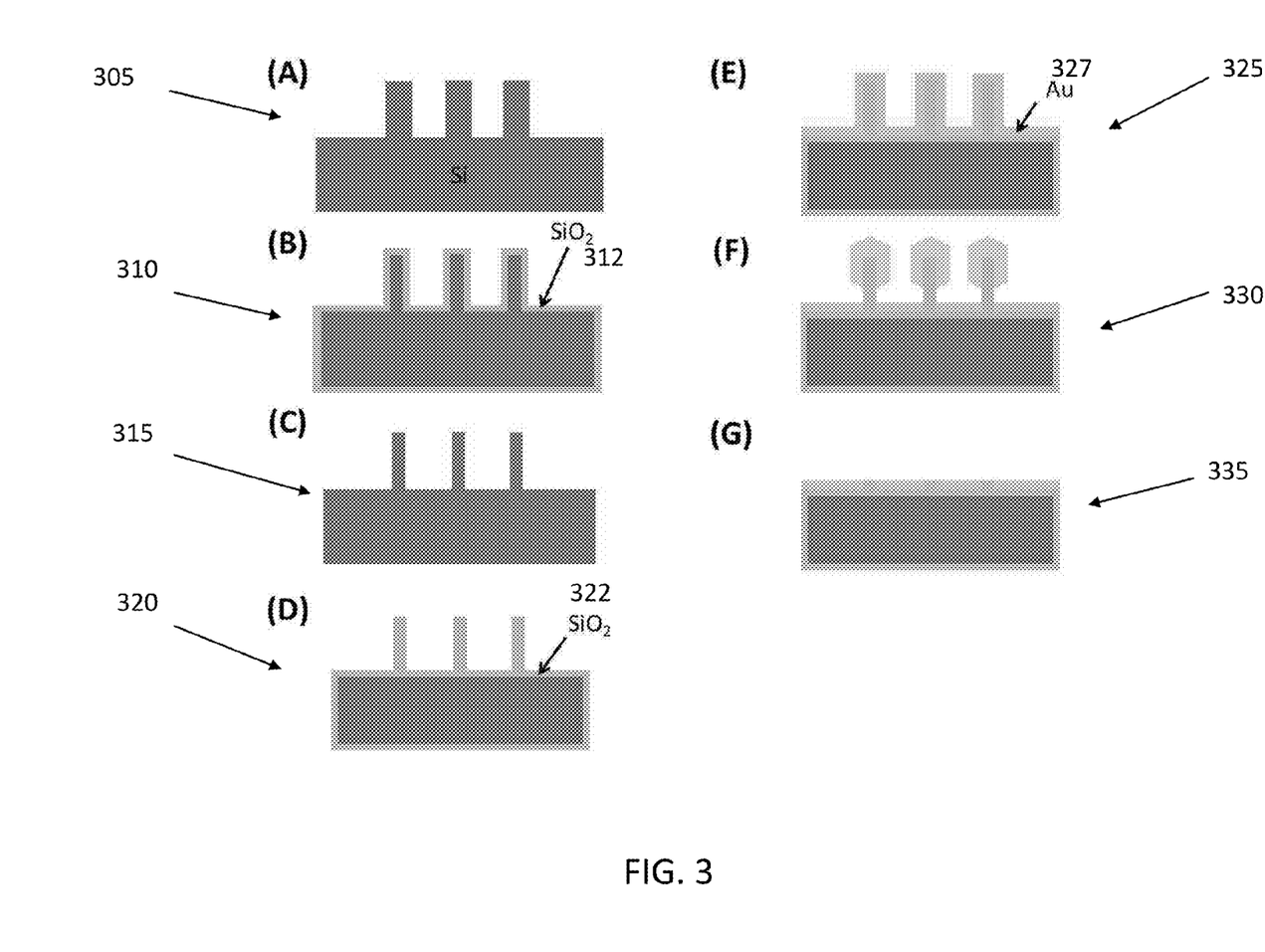
FIG. 3 illustrates a method of fabrication of nanostructures on Si substrates.

The method described above can also be applied to nano-apertures on metal films as in FIG. 3 (335). For this embodiment, as visible in FIG. 4, the chip is coated (430) with a sacrificial layer (432) and a carrier chip (433). In subsequent steps, a fabrication flow similar as to what described above can be followed to obtain nano-apertures on a flexible layer as in (435). The nano-apertures can be fabricated, in some embodiments, by chemically or mechanically removing the protruding nanostructures in (435), leaving nano-tunnels apertures between the metallic layers. Regarding the embodiment with metal nanospheres on pillars, the option is available to choose whether to keep the metal layer on the background or not.

Figure 5:
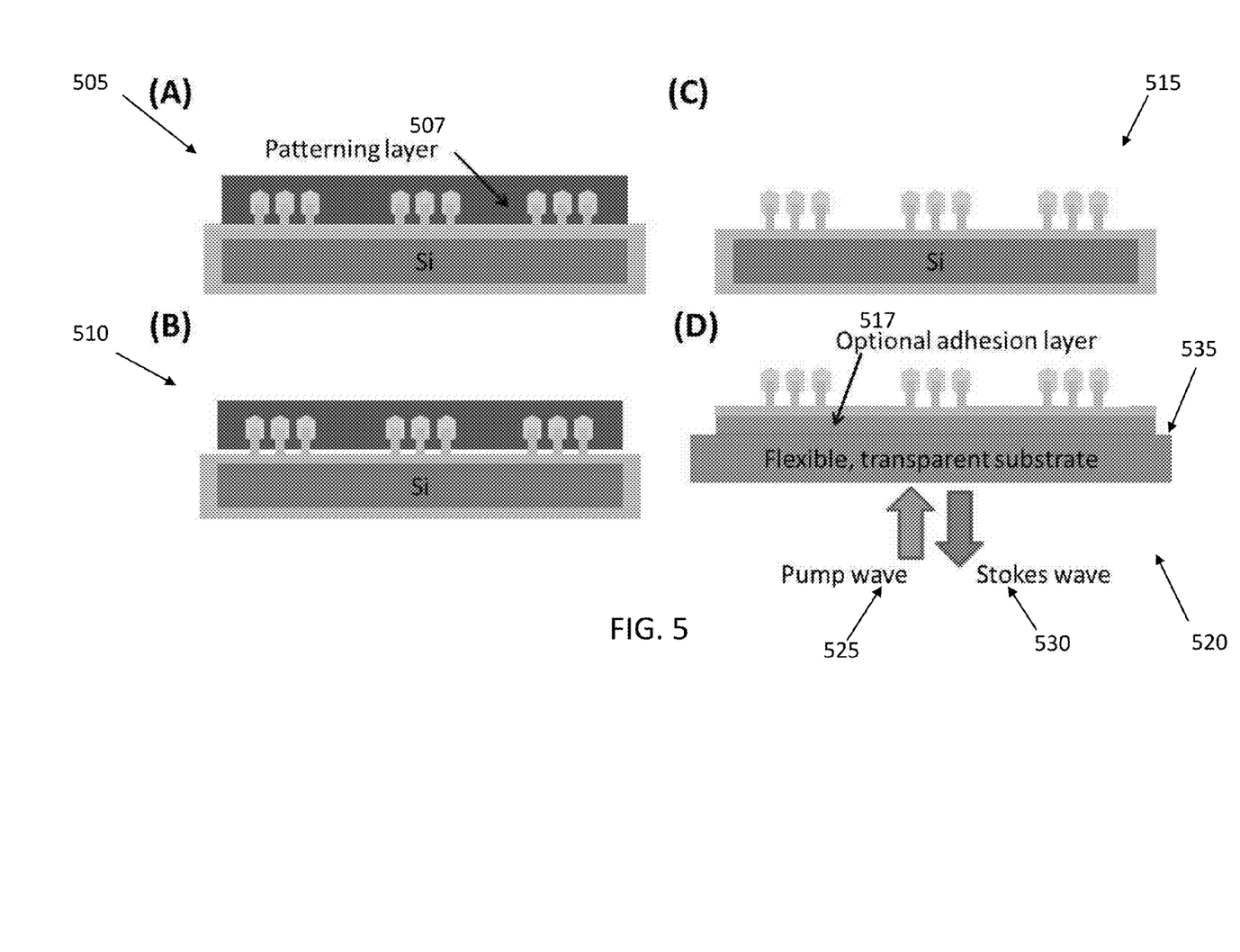
FIG. 5 illustrates a method of fabrication with a patterning layer.

In some embodiments, referring to FIG. 5 (505), a patterning layer (507) can be spin-coated onto the chip to protect the nanospheres. In some embodiments, a photoresist can be used, but it is also possible to employ other materials that can be patterned (by lift-off, etc) and subsequently removed. An etch method can be chosen to remove the bottom metal layer without compromising the patterning layer (510). In some embodiments, a Gold Etchant TFA can be used. The patterning layer (507) is then removed by either wet chemistry or plasma etching (515), and the entire chip can then undergo the fabrication procedures as described above, to be transferred onto a flexible substrate (535). The substrate can be chosen to be transparent in the spectral region of interest, so that optical excitation can be transmitted through for a readout. An example of an optical technique is to excite the final structure from the backside with a laser beam, and detect the scattered Raman signals (520). For example, a pump wave will be in the direction (525) and Stokes wave will be received in the direction (530). An optional adhesive layer (517) can also be used.

Figure 6:
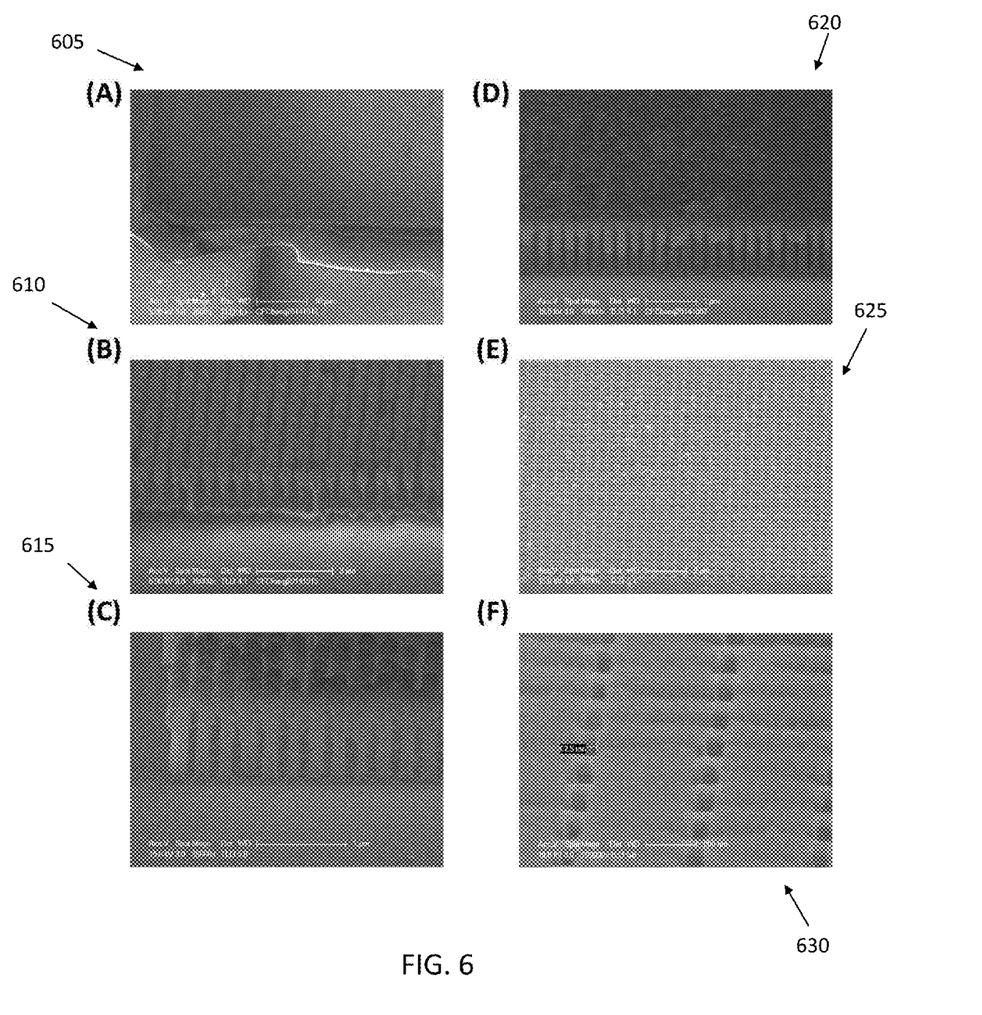
FIG. 6 illustrates other SEM images of nanostructures.

FIG. 6 (605) shows an example of SERS structures transferred onto a flexible substrate (PDMS in this embodiment), and FIG. 6 (610) is a close-up verifying the integrity of transferred structures. FIG. 6 (615) and (620) demonstrate the removal of a bottom Au region while keeping the SERS nanospheres intact, thus corroborating the method of FIG. 5. For nano-apertures, FIG. 6 (625) shows an example of such fabrication on a 200 nm Au layer, and FIG. 6 (630) is an exemplary structure starting from the same Si template on a 200 nm Al layer.

Figure 7:
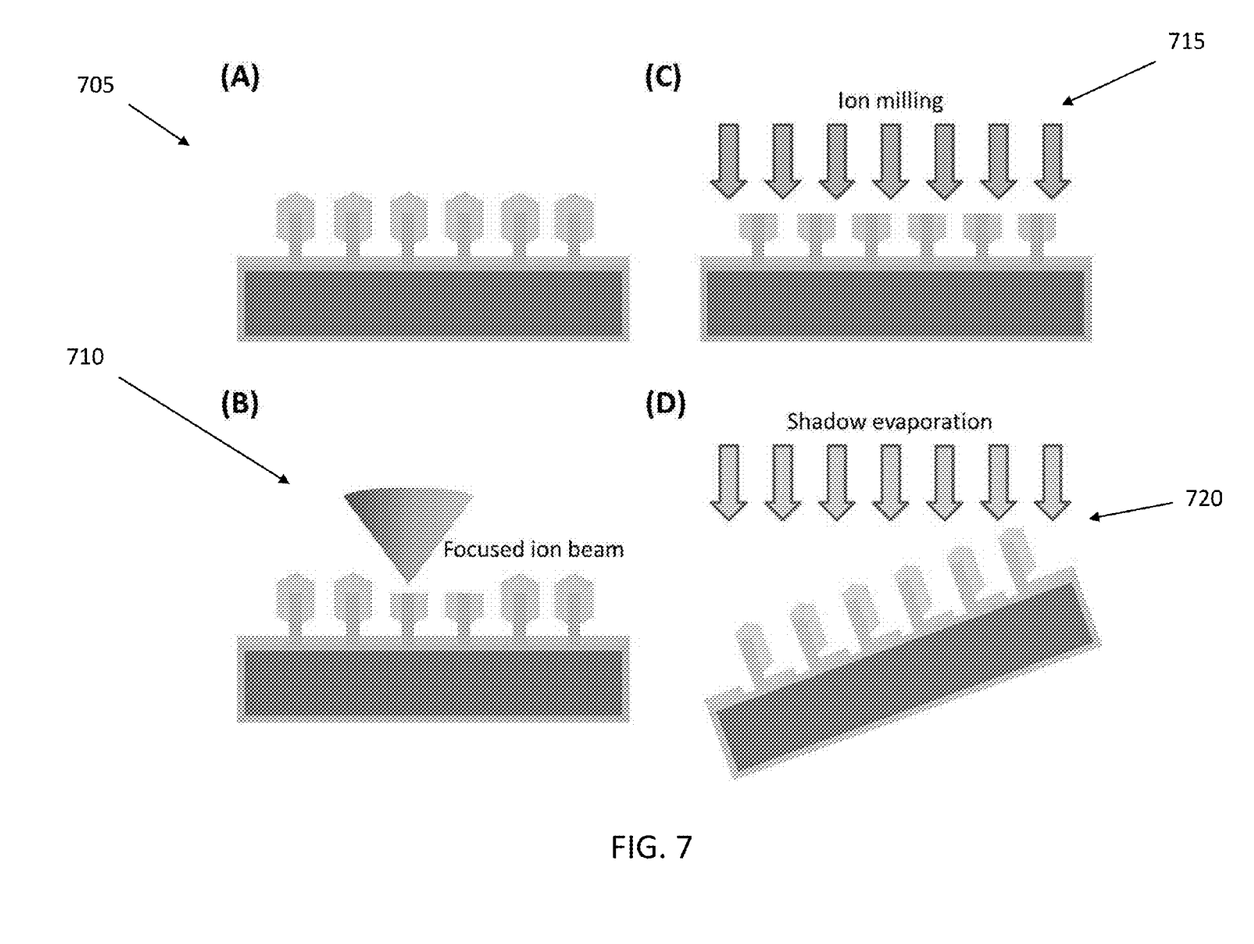
FIG. 7 illustrates methods of patterning nanostructures.

For SERS structures, the metal nanospheres can be further modified before being transferred to flexible substrates. For example, starting from reflowed structures as in FIG. 7 (705), it is possible to use techniques like focused ion beam (FIB) to reshape the nanospheres topically (710). In other embodiments (715), it is possible to reshape all the nanostructures with techniques like ion milling. In both cases the substrate can be tilted so that the nanostructures are reshaped at specific angles; the reshaping procedures can be carried out in multiple steps at different angles each time, for more sophisticated sculpting. For example, starting from oxidized nanostructures (FIG. 1, 110), it is possible to tilt the substrate for shadow evaporation so that metals are deposited at a specific angle (FIG. 7, 720). Several deposition runs can take place at a different tilt angle each time. After deposition, the nanostructures can optionally go through further reshaping (710, 715), also at different angles for each step. The structures can then be transferred as described above.

Figure 8:
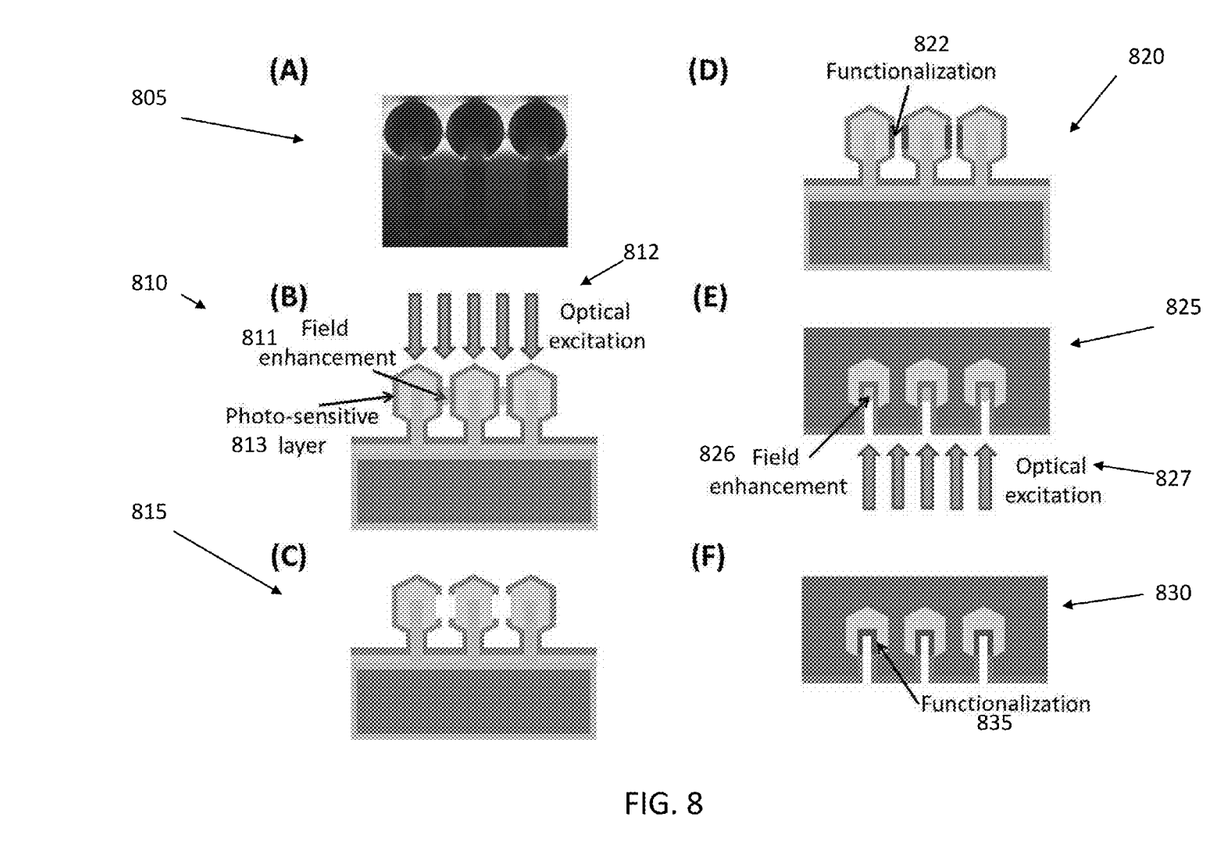
FIG. 8 illustrates a method of fabrication for localized functionalization.

When the SERS nanostructures are functionalized for binding-specific applications, it is possible to take advantage of local field enhancements to achieve self-aligned functionalization. Referring to FIG. 8 (805), finite-difference time-domain (FDTD) simulations verifies the local field enhancement between metal nanostructures. If the entire chip is coated (810) with photo-sensitive materials (813), the illumination intensity (812) can be chosen so that the exposure is below the threshold of photo-reaction except at the hot spots where the optical fields are locally enhanced (811). If the photo-reaction is chemical, these exposed parts can be developed for removal. In the case of ablation, these regions are burned away in the fabrication process. Local spots of metal nanostructures are then again exposed (815), and these areas can be functionalized in a self-aligned manner (820) where there will be hot spots again during the SERS detection. Therefore, in some embodiments the functionalization is localized in the hotspots (822). Similarly, for nanocups (as in FIG. 1, 130, 132 and 140) it is possible to achieve self-aligned functionalization within the interiors of the cups. For example, for the configuration (825), after the application of a photo-sensitive layer and illumination (827) at controlled optical intensities, the areas with local field enhancement (826) will again be exposed by either development or ablation. The inside of the nanocups can be functionalized (830). Detection techniques that take advantage of a small distance between molecules, such as Förster resonance energy transfer (FRET), can be used in these embodiments.

Figure 9:
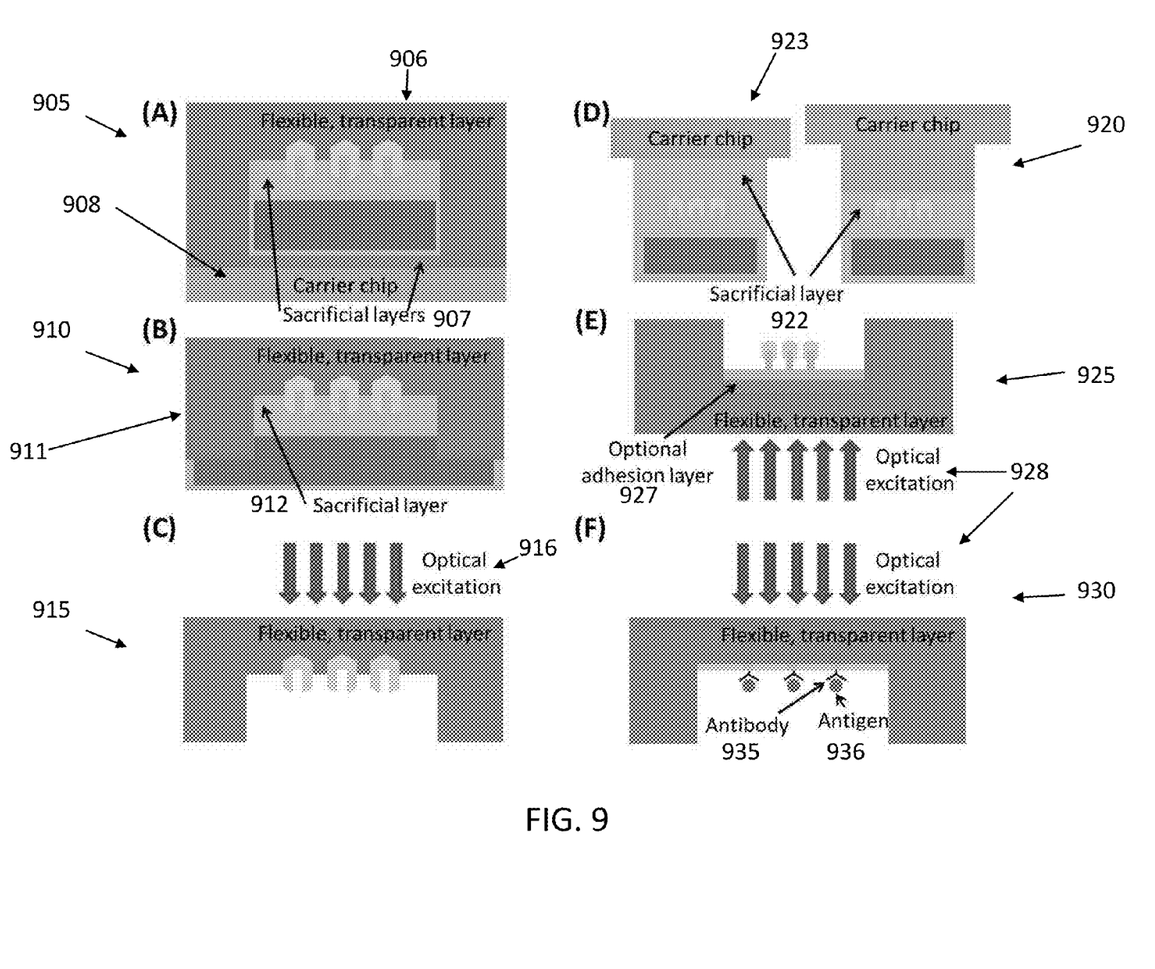
FIG. 9 illustrates another method of fabrication of nanostructures.

In several embodiments, it is possible to transfer the plasmonic structures into the recess of a cavity as in FIG. 9. In FIG. 9 (905), the chip is mounted on a carrier substrate (908) before a flexible layer (906) is deposited. Sacrificial layers (907) can be used. In another embodiment (910), on the other hand, it is possible to etch into the regions outside of the nanostructures, either prior to the nanofabrication (i.e., the nanostructures would be fabricated on the mesa regions of the chip) or after (i.e., the area of plasmonic structures are protected with a masking material during the etch), before eventually applying a flexible layer (911). Sacrificial layers (912) can be used. After the removal of unwanted regions, it is possible to obtain SERS structures inside of a cavity (915). In some embodiments, optical excitation can be applied (916) during measurements.

In some embodiments, the device can be used as a sticker, which can adhere conformally to a surface of interest such as human skin, endoscopic probe, etc. An exemplary application would be wearable SERS sensors for clinical purposes. To transfer the metal nanostructures with the pillars, a sacrificial layer (922) can be used. In some embodiment, the structure can be fabricated with a thick sacrificial layer (923) or an etched carrier chip (920). For subsequent optical illumination from the back side, the metal in these embodiments is already removed, except for the nanospheres on top of the pillars.

Following similar steps as in FIG. 4, it is possible to obtain SERS nanostructures in a flexible cavity as in FIG. 9 (925). Starting from structures similar to that in FIG. 3 (335) or FIG. 4 (430), with similar fabrication procedures it is possible to transfer nano-apertures as depicted in FIG. 9 (930). In this embodiment, the glass nano-openings (nano-tunnels) can be functionalized (935, 936) for a plasmonic assay for optical readout.

Figure 10:
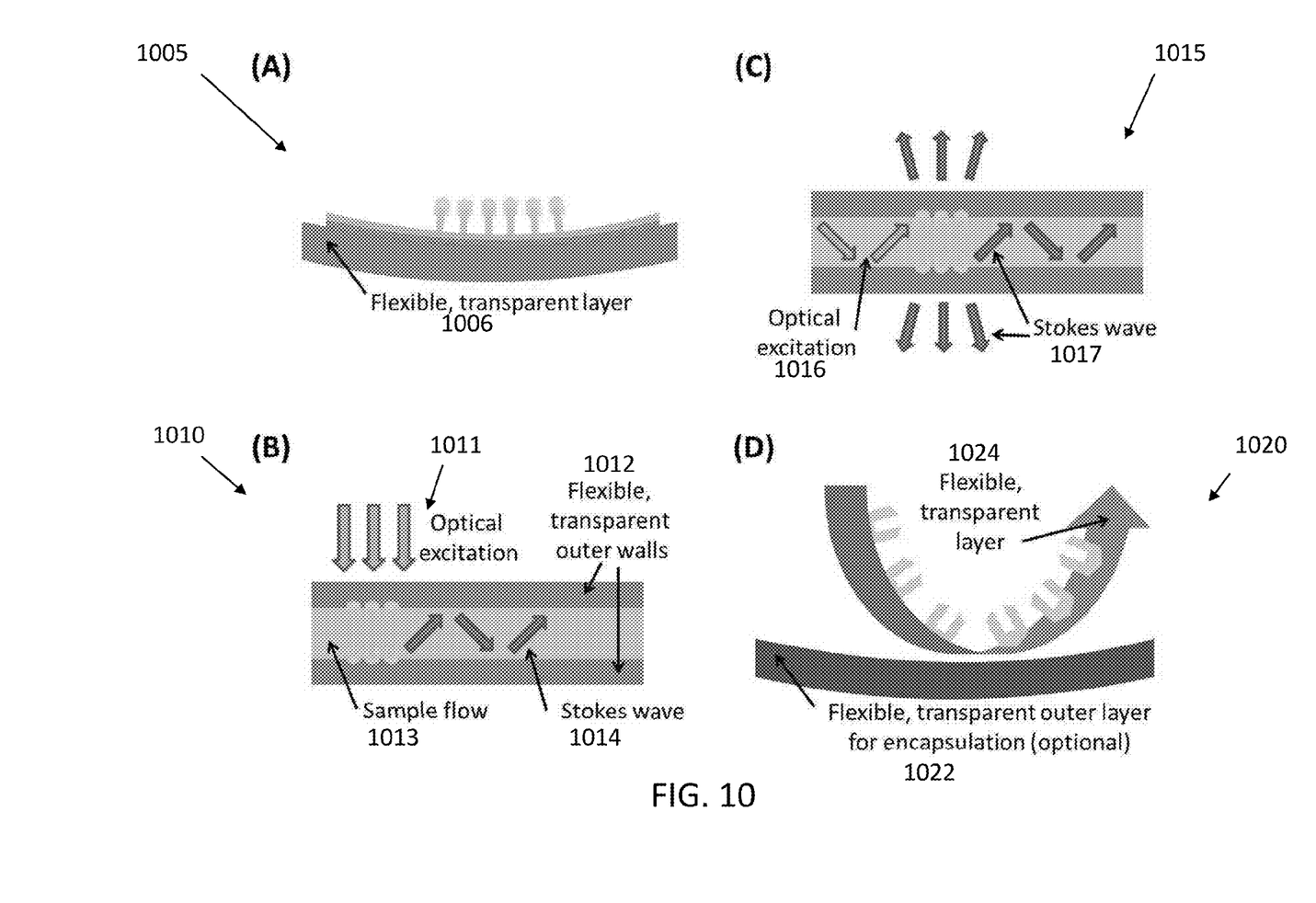
FIG. 10 illustrates a method of fabrication for rolled flexible substrates.

In some embodiments, as visible in FIG. 10, a flexible substrate (1006) can be bent so that the SERS structures are on the inwardly-curved side of the channel (1005); this embodiment has the added benefit that the nanostructures can be even closer to each other. Furthermore, it is possible to roll the flexible layer (1012) into a tube (1010). The core region can not only accommodate fluid sample flows (1013) but also serve as a waveguide due to the difference in refractive index relative to the sidewalls. After optical excitation (1011) through the transparent sidewalls (1012), some Stokes waves (1014) would propagate along the channel for subsequent collection and detection.

In some embodiments (1015), the channel can also function as a waveguide for the pump waves (1016), resulting in Stokes waves (1017) scattering through the sidewalls or propagating along the channel for detection. In other embodiments, with proper designing and cutting of nanostructures on a flexible layer (1024), the strip can be rolled into a tube in a spiral fashion to extend the effective interaction area (1020). These rolled substrates can also host pillar nanostructures instead of nanocups. An optional layer, also flexible and transparent (1022), can be wrapped on the outside for hermetic sealing if necessary. In other words, the flexible layer is rolled in a spiral fashion to form a cylindrical tube. In some exemplary embodiments (1010, 1015, 1020) it is possible to use nanocups, but other embodiments, such as (1005) are also feasible with stretched substrates, if the regions outside the nanostructures are etched into zig-zagging patterns, as it has been done in the literature for stretchable electronics, see Ref. [8].

The present disclosure describes wafer-scalable methods, available in commercial semiconductor foundries for mass production, for making plasmonic nanostructures and transferring them onto flexible substrates. In several embodiments, polydimethylsiloxane (PDMS) is used for demonstration purposes, but other options can include, and are not limited to, polymer, plastics, etc.

A flexible layer can be deposited on top of the nanostructures, followed by separation from the semiconductor substrate either through mechanical peel-off or chemical etching that does not affect the flexible materials. Nanocups with an arbitrary shape of cross section and a high aspect ratio, with optional 3D sculpting, can be mass-fabricated in this manner. By controlling the thermal reflow process, it is also possible to fine-tune the shapes of these nanocups before their transfer onto flexible substrates.

It is possible to optionally remove the metal in the open areas between nanostructures, resulting in the choice of a blank or metal background.

With the application and treatment of a sacrificial layer before the transfer, it is possible to control how deeply embedded the nanostructures are in the flexible layer. For Raman applications, such structures can have hot spots not only within the nanocups but also between adjacent nanocups.

The flexible substrate can be stretched or compressed to adjust the distance between nanostructures externally.

By controlling the oxidation process so that the Si nanostructures are not oxidized through, the outer $SiO_2$ layer can be removed before further oxidation to achieve even smaller structures than allowed by the lithography resolution.

The structures can be first attached to a carrier chip with a sacrificial layer to facilitate the removal of the original substrate, and the nanostructures can then be transferred onto a flexible layer in an upright position. An optional adhesion layer can be used between the nanostructures and the flexible substrate.

For metal nanostructures on top of $SiO_2$ pillars, it is possible to preserve these nanostructures with masking while removing the metal layer in the general background. In this way the optical excitation can come from the other side of the membrane.

It is possible to modify the reflowed metal nanostructures, either locally through techniques like focused ion beam (FIB), or globally like ion milling. In both cases the substrate can be tilted for more variation, and several runs of reshaping can take place at different angles. The structures can then be transferred to flexible substrates as described.

The metal deposition step can also be done at an angle as in shadow evaporation, and again several subsequent deposition steps can be carried out at different angles, followed by various reshaping procedures, also optionally at different angles. The final structures can then be transferred to flexible substrates.

Since local fields are enhanced at Raman hot spots, it is possible to first coat the entire chip with photo-sensitive materials, and expose the chip to controlled intensities of illumination, so that only materials around the hot spots are photo-activated. These regions can be removed either by ablation or by subsequent development, and can be functionalized in this self-aligned manner. A similar fabrication process can be applied to nanocup structures. These functionalized sites can facilitate detection techniques such as Förster resonance energy transfer (FRET).

With a carrier substrate, or by etching into the original semiconductor substrate, it is possible to create a recess in the final flexible substrate with plasmonic nanostructures on the inside. Such a device can be implanted or used as a conformal sticker onto a surface such as human skin for wearable applications. If nano-apertures are used, they can be functionalized accordingly.

It is possible to bend the flexible substrates so that the metal nanostructures are closer to each other. The flexible layer can also be rolled into a tube. In some embodiments the central region can function not only as a sample flow channel but also as an optical waveguide. For waveguide purposes, the excitation electromagnetic waves can either come through the transparent sidewall or propagate along this central waveguide. The signal waves to be detected can either propagate along the waveguide or scatter through the sidewall for subsequent detection.

The nanostructures and the flexible layer can be designed in such a manner that they can be rolled up in a spiral fashion for extended interaction area. An optional outer layer can be coated for sealing if necessary.

Therefore, in some embodiments, the fabrication methods of the present disclosure comprise etching a silicon substrate to form silicon nanostructures on top of the silicon substrate; oxidizing the silicon nanostructures to form silicon oxide nanostructures; depositing a metallic layer on the silicon oxide nanostructures; reflowing the metallic layer to form metallic bulbs on a top section of the silicon oxide nanostructures; depositing a continuous flexible substrate on the metallic bulbs and on the silicon oxide nanostructures; and removing the silicon substrate and the silicon oxide nanostructures.

In other embodiments, the fabrication methods of the present disclosure comprise etching a silicon substrate to form silicon nanostructures on top of the silicon substrate; oxidizing the silicon nanostructures to form silicon oxide nanostructures; depositing a metallic layer on the silicon oxide nanostructures and on the silicon substrate between the silicon oxide nanostructures; reflowing the metallic layer to form metallic bulbs on a top section of the silicon oxide nanostructures while leaving parts of the metallic layer on the silicon substrate between the silicon oxide nanostructures; removing the silicon oxide nanostructures by etching or mechanical methods to form nano-apertures between the parts of the metallic payer on the silicon substrate; depositing a continuous sacrificial layer on the nano-apertures; attaching a carrier chip to the continuous sacrificial layer; removing the silicon substrate by etching; depositing a continuous flexible substrate on a surface of the nano-apertures opposite to a surface with the continuous sacrificial layer; and removing the continuous sacrificial layer and the carrier chip.

In yet other embodiments, the fabrication methods of the present disclosure comprise etching a silicon substrate to form silicon nanostructures on top of the silicon substrate; oxidizing the silicon nanostructures to form silicon oxide nanostructures; depositing a metallic layer on the silicon oxide nanostructures; reflowing the metallic layer to form metallic bulbs on a top section of the silicon oxide nanostructures; depositing a photosensitive layer on the metallic bulbs and on the silicon oxide nanostructures; selecting an intensity for optical excitation to be above an excitation threshold only for the photosensitive layer between the metallic bulbs; optically exciting at the selected intensity; removing the excited photosensitive layer, thereby leaving gaps in the photosensitive layer between the metallic bulbs; and functionalizing the gaps between the metallic bulbs. In some embodiments, an adhesive layer can be attached to some parts of the flexible substrate so that the device can be attached as a flexible sticker.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] S. Walavalkar et al., "Scalable Method for the Fabrication and Testing of Glass-Filled, Three-Dimensionally Sculpted Extraordinary Transmission Apertures," *Nano Lett.* 14 (1), pp. 311-317 (2014).
[2] C.-F. Chang et al., "Plasmonics Nanostructures for Multiplexing Implantable Sensors," U.S. Ser. No. 61/938,784, provisional application filed Feb. 12, 2014.
[3] S. Walavalkar et al., "Reflowed Gold Nanostructures for Surface Enhanced Raman Spectroscopy and Related Inventions," U.S. Publication No. 2015/0223738, published on Aug. 13, 2015.
[4] J. C. Lo et al., "Fabrication of a large, ordered, three-dimensional nanocup array," *App. Phys. Lett.* 101 (8), p. 081109 (2012)
[5] Z. Wang et al., "Synthesis and magnetic properties of large-area ferromagnetic cylindrical nanoshell and nanocup arrays," *J. App. Phys.* 113 (21), p. 214301 (2013)
[6] M. Frederiksen et al., "Plasmon Hybridization and Field Confinement in Multilayer Metal-Dielectric Nanocups," *J. Phys. Chem.* 117, pp. 15782-15789 (2013)
[7] Y. K. Mishra et al., "Formation of Self-organized Silver Nanocup-Type Structures and Their Plasmonic Absorption," *Plasmonics* 8, pp. 811-815 (2013)
[8] D.-H. Kim et al., "Flexible and Stretchable Electronics for Biointegrated Devices," *Annu. Rev.* 14, pp. 113-128 (2012).

What is claimed is:

1. A method comprising:
   etching a silicon substrate to form silicon nanostructures on top of the silicon substrate;
   oxidizing the silicon nanostructures to form silicon oxide nanostructures;
   depositing a metallic layer on the silicon oxide nanostructures;
   reflowing the metallic layer to form metallic bulbs on a top section of the silicon oxide nanostructures;
   depositing a continuous flexible substrate on the metallic bulbs and on the silicon oxide nanostructures; and
   removing the silicon substrate and the silicon oxide nanostructures.

2. The method of claim 1, wherein the nanostructures are pillars.

3. The method of claim 1, wherein the metallic layer is Au.

4. The method of claim 1, wherein the continuous flexible substrate is polydimethylsiloxane.

5. The method of claim 1, further comprising depositing a sacrificial layer between the silicon oxide nanostructures and the continuous flexible substrate.

6. The method of claim 1, wherein the continuous flexible substrate is transparent to optical waves.

7. The method of claim 1, further comprising reshaping the metallic bulbs prior to depositing the continuous flexible substrate.

8. The method of claim 7, wherein reshaping comprises applying a focused ion beam with a different intensity for at least two metallic bulbs.

9. The method of claim 7, wherein reshaping comprises ion milling the metallic bulbs.

10. The method of claim 7, wherein reshaping comprises shadow evaporating at an angle.

11. The method of claim 10, wherein shadow evaporating at an angle comprises shadow evaporating at an angle in successive steps, each step being at a different angle.

12. The method of claim 1, further comprising bending the continuous flexible substrate with the nanostructures being on a concave side of the continuous flexible substrate.

13. The method of claim 12, wherein bending the continuous flexible substrate comprises bending the continuous flexible substrate in a cylinder shape.

14. The method of claim 13, wherein bending the continuous flexible substrate is carried out in a spiral fashion.

15. The method of claim 13, wherein the continuous flexible substrate rolled in the cylinder shape is configured to contain a fluid sample flow within.

16. The method of claim 15, wherein the continuous flexible substrate rolled in the cylinder shape is further configured to act as a waveguide for optical waves.

17. A method comprising:
etching a silicon substrate to form silicon nanostructures on top of the silicon substrate;
oxidizing the silicon nanostructures to form silicon oxide nanostructures;
depositing a metallic layer on the silicon oxide nanostructures and on the silicon substrate between the silicon oxide nanostructures;
reflowing the metallic layer to form metallic bulbs on a top section of the silicon oxide nanostructures while leaving parts of the metallic layer on the silicon substrate between the silicon oxide nanostructures;
removing the silicon oxide nanostructures to form nano-apertures between the parts of the metallic layer on the silicon substrate;
depositing a continuous sacrificial layer on the nano-apertures;
attaching a carrier chip to the continuous sacrificial layer;
removing the silicon substrate by etching;
depositing a continuous flexible substrate on a surface of the nano-apertures opposite to a surface with the continuous sacrificial layer; and
removing the continuous sacrificial layer and the carrier chip.

18. The method of claim 17, further comprising inserting an adhesive layer between the continuous flexible substrate and the surface of the nano-apertures opposite to a surface with the continuous sacrificial layer, and wherein the removing the silicon oxide nanostructures is by etching or mechanical removal.

19. The method of claim 17, wherein the nanostructures are pillars.

20. The method of claim 17, wherein the metallic layer is Au.

21. The method of claim 17, wherein the continuous flexible substrate is polydimethylsiloxane.

22. The method of claim 17, further comprising depositing a sacrificial layer between the silicon oxide nanostructures and the continuous flexible substrate.

23. The method of claim 17, wherein the continuous flexible substrate is transparent to optical waves.

24. The method of claim 17, wherein removing the silicon oxide nanostructures to form nano-apertures comprises controlling a depth at which the nano-apertures are formed.

25. A method comprising:
etching a silicon substrate to form silicon nanostructures on top of the silicon substrate;
oxidizing the silicon nanostructures to form silicon oxide nanostructures;
depositing a metallic layer on the silicon oxide nanostructures;
reflowing the metallic layer to form metallic bulbs on a top section of the silicon oxide nanostructures;
depositing a photosensitive layer on the metallic bulbs and on the silicon oxide nano structures;
selecting an intensity for optical excitation to be above an excitation threshold only for the photosensitive layer between the metallic bulbs;
optically exciting at the selected intensity;
removing the excited photosensitive layer, thereby leaving gaps in the photosensitive layer between the metallic bulbs; and
functionalizing the gaps between the metallic bulbs.

26. The method of claim 25, further comprising an adhesive layer attached to the continuous flexible substrate on a surface opposite the nanostructures.

* * * * *

UNITED STATES PATENT AND TRADEMARK OFFICE
CERTIFICATE OF CORRECTION

PATENT NO. : 9,512,000 B2
APPLICATION NO. : 14/952876
DATED : December 6, 2016
INVENTOR(S) : Chieh-feng Chang et al.

Page 1 of 1

It is certified that error appears in the above-identified patent and that said Letters Patent is hereby corrected as shown below:

In the Specification

Column 1, After Line 20, and Before the header "TECHNICAL FIELD" under Column 1, Line 22, ADD a Government Support Clause as follows:
"STATEMENT OF GOVERNMENT GRANT
This invention was made with government support under Grant No. HR0011-15-2-0050 awarded by DARPA. The government has certain rights in the invention."

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*